(12) United States Patent
Avendano et al.

(10) Patent No.: US 6,511,657 B2
(45) Date of Patent: Jan. 28, 2003

(54) TWO-PHASE ROLL-ON COSMETIC PRODUCT

(75) Inventors: Esther Avendano, Mexico (MX); Adriana Urrutia-Gutierrez, Mexico (MX); Wilson Lee, Bloomfield, NJ (US); Xiaozhong Tang, Bridgewater, NJ (US)

(73) Assignees: Colgate-Palmolive Company, New York, NY (US); Dow Corning Corporation, Midland, MI (US)

( * ) Notice: Subject to any disclaimer, the term of this patent is extended or adjusted under 35 U.S.C. 154(b) by 0 days.

(21) Appl. No.: 09/838,802

(22) Filed: Apr. 20, 2001

(65) Prior Publication Data

US 2002/0155078 A1 Oct. 24, 2002

(51) Int. Cl.⁷ .............................. A61K 7/32; A61K 7/00; A61K 7/34; A61K 7/38; A61K 7/021
(52) U.S. Cl. .......................... 424/65; 424/401; 424/486; 424/66; 424/67; 424/68; 424/78.02; 514/63; 514/724; 514/770; 514/947; 524/862
(58) Field of Search .......................... 424/401, 65, 496, 424/66, 67, 68, 78.02; 524/862; 514/63, 770, 724, 947

(56) References Cited

U.S. PATENT DOCUMENTS

| | | |
|---|---|---|
| 4,021,152 A | 5/1977 | Toyoda |
| 4,030,844 A | 6/1977 | Lench et al. |
| 4,033,700 A | 7/1977 | Spatz |
| 4,120,948 A | 10/1978 | Shelton |
| 4,438,095 A | 3/1984 | Grollier et al. |
| 4,767,741 A | 8/1988 | Komor et al. |
| 4,973,473 A | 11/1990 | Schneider et al. |
| 4,980,155 A | 12/1990 | Shah et al. |
| 5,213,799 A | 5/1993 | Goering et al. |
| 5,290,555 A | 3/1994 | Guthauser et al. |
| 5,474,777 A | 12/1995 | Marion et al. |
| 5,553,957 A | 9/1996 | Dornbusch et al. |
| 5,593,663 A | 1/1997 | Leng et al. |
| 5,654,362 A * | 8/1997 | Schulz et al. ............... 424/401 |
| D402,550 S | 12/1998 | Poisson |
| 5,919,437 A | 7/1999 | Lee et al. |
| 5,922,308 A * | 7/1999 | Brewster et al. ............ 424/400 |
| 6,019,991 A | 2/2000 | Tanaka et al. |
| 6,132,126 A | 10/2000 | Sheffler et al. |
| 6,180,587 B1 | 1/2001 | Fuller et al. |

FOREIGN PATENT DOCUMENTS

| | | |
|---|---|---|
| WO | WO 91/08732 | 6/1991 |
| WO | WO 01/03541 A1 | 1/2001 |

* cited by examiner

*Primary Examiner*—Frederick Krass
*Assistant Examiner*—Clinton Ostrup
(74) *Attorney, Agent, or Firm*—Rosemary M. Miano; James DeCesare

(57) ABSTRACT

A two-phase roll-on antiperspirant and/or deodorant is described which comprises: (a) a clear, translucent or opaque non-polar phase having a viscosity in the range of 20 cps–9,000 made by combining: a cross-linked or partially cross-linked non-emulsifying siloxane elastomer; 0.1–70 weight % of one or more low viscosity, lipophilic emollients; (b) a clear, translucent or opaque polar phase have a viscosity in the range of 20–9,000 cps made by combining: one or more members selected from the group consisting of water, glycols and polyhydric alcohols; and an antiperspirant active salt which is soluble or suspendible in the polar phase; wherein the polar phase comprises (i) a sufficient amount of water, glycols or polyhydric alcohols to dissolve or suspend the antiperspirant active, and (ii) optionally may comprise up to 30 weight % water; up to 16.00 weight % of ethyl alcohol; up to 16 weight % isopropyl alcohol; or mixtures of the foregoing; (iii) 0.1–2.5 weight % of a water soluble cationic derivative selected from the group consisting of hydroxyethyl cellulose and its copolymers provided that the viscosity of the polar phase does not exceed 9,000 cps.

38 Claims, No Drawings

TWO-PHASE ROLL-ON COSMETIC PRODUCT

FIELD OF THE INVENTION

This invention relates to a two-phase, roll-on cosmetic product, especially for use in the field of antiperspirants and/or deodorants.

BACKGROUND OF THE INVENTION

Current roll-on products in the market are usually emulsions which involve emulsions and/or the suspension of an antiperspirant active in the formulation. The products frequently require the use of one or more surfactants to stabilize and/or compatabilize two non-compatible phases. There are two issues associated with the use of surfactants. The first issue is skin irritation. Unless the surfactant system is carefully selected, the use of such materials may cause skin irritation. The second issue is efficacy. It may be the case that in some systems, the use of a surfactant may interfere with the gel plug formation by which many antiperspirant actives work to reduce perspiration.

Another group of benefits may also be achieved with the reduction and/or elimination of surfactants in cosmetic products that contain an antiperspirant active. These benefits include improving the dry feel of the product, reducing the amount of non-white residue on skin and clothing, and reducing the tackiness of the product.

Two-phase systems have been seen in a few cosmetic applications including liquids and solids. One commercial liquid two-phase product from The Dial Corporation (Scottsdale, Ariz.) is Nature's Accents® Bath Treats, a bubble bath product comprising water, cetearyl ethylhexanoate, sodium laureth sulfate, cocamidopropyl betaine, fragrance, glycerin, sodium cocoyl glutamate (and) disodium cocoyl glutamate, PEG-8, DMDM hydantoin, tetrasodium EDTA, hydrolyzed milk protein, honey extract, and coloring agents. As a cleansing material this product is formulated with surfactants. This product has a creamy milky top layer with a clear colored layer under it.

A second commercial liquid two-phase product is Cloud Dance™ breeze cologne spray distributed by CCA Industries, Inc. (East Rutherford, N.J.). This product lists the following ingredients: SD alcohol, 40D, hexamethyldisiloxane, fragrance, distilled water, sodium chloride, coloring agents, and benzophenone-3. This product is clear with two bands of differing colors.

There are patent references that describe two-phase or multiphase technology. U.S. Pat. No. 4,120,948 to Shelton describes a two-phase stick antiperspirant having (1) a substantially anhydrous antiperspirant phase comprising a water-insoluble, high melting point wax, a liquid emollient, and high levels of a particulate, antiperspirant active material and (2) a gel phase comprising a polyhydric alcohol gelled with either a fatty acid soap or a fatty acid amide.

U.S. Pat. No. 4,438,095 to Grollier et al describes a liquid cosmetic composition comprising two separate liquid phases. The first phase is an aqueous phase in which at least one cationic polymer is dissolved. The composition contains no detergent agent or foaming agents.

U.S. Pat. No. 4,767,741 to Komor et al teaches a two-phase liquid cosmetic composition comprising an oil phase, and organic liquid/water phase and insoluble solid particles absorbed on the interface between the two phases, wherein the solid particles are the in situ precipitation product of at least a first salt solution and a second salt solution (added to the oil phase and organic/water phase during blending thereof).

U.S. Pat. No. 4,973,473 to Schneider et al teaches (in a preferred embodiment) a composition comprising two discrete gel phases. The composition includes an emollient complex containing a selected carboxylic acid amide(s), a mucopolysaccharide, at least one skin structuring protein and an astringent.

U.S. Pat. No. 4,980,155 to Shah et al teaches a two-phase cosmetic composition comprising a color phase which includes a first phase comprising a film forming agent, at least one colorant, an emulsifier and water; and a second phase comprising a gel phase comprising a water soluble polymer and water. The phases are miscible with each other but are disposed in discrete side by side separate phases.

U.S. Pat. No. 5,213,799 to Foring et al describes skin treating compositions which comprise a transparent oil phase and a transparent aqueous phase, preferably with humectant effect, which permits a homogenous mixture when shaken together and thereafter separates again into two transparent phases. The cosmetic composition includes the use of 0.1–1.0 weight % of C12–C18 fatty acid triglycerol ester.

U.S. Pat. No. 5,290,555 to Guthauser et al teaches compositions with structural color in which two phases are selected with the same refractive index but different dispersive power. Either or both of the phases may contain cosmetically active ingredients.

U.S. Pat. No. 5,474,777 to Marion et al describes liquid cleansing compositions consisting of an oily phase and an aqueous phase, wherein the oily phase consists of at least one dialkylphosphate and, optionally, products miscible therein, and the aqueous phase contains one or more ionic surfactants.

U.S. Pat. No. 5,593,663 to Leng et al describes antiperspirant actives which are amphiphilic materials that, upon contact with perspiration, form a water-insoluble liquid crystal phase of greater than one-dimensional periodicity.

U.S. Pat. No. 5,654,362 to Schultz et al describes silicone oils and solvents thickened by silicone elastomers and suitable for use in products such as antiperspsirants and deodorants.

U.S. Pat. No. 5,919,437 to Lee et al describes solid cosmetic compositions including cosmetic cream compositions containing silicone elastomers as gelling agents.

U.S. Phase 6,019,991 to Tanaka et al teaches a two-phase cosmetic composition comprising separate and distinct oil and aqueous phases which form a highly temporary clear emulsion when shaken together. A clear package is used. One phase may be colored while the other is usually water white.

U.S. Pat. No. 6,180,587 to Fuller et al teaches a multiple phase composition comprising a lower aqueous phase comprising at least 1 weight % of a polymer or copolymer selected from the group consisting of polyacrylate, polystyrene sulfonate, polyvinyl-pyrrolidone, maleic anhydride and mixtures thereof and an upper aqueous phase having a cleansingly effective amount of a surfactant.

PCT case WO 00/67712 discloses a solid stick containing antiperspirant actives and formed with a core phase and an outer phase.

Conventional roll-on products used as antiperspirants and/or deodorants are usually emulsions or anhydrous suspensions. Emulsions can be oil-in-water or water-in-oil systems wherein one phase is dispersed in the other. In emulsions both phases remain together because of the addition of surfactants. Emulsion products tend to have a wet feel, a higher level of tackiness and some irritation issues. Anhydrous suspensions are composed of powders suspended in anhydrous liquids. They typically include a relatively high percentage of suspending agents that contribute to white residues being left on skin and clothing. While the anhydrous suspension do not produce a wet feel, they exhibit other problems such as settling of the powder over time and leakage of the carrier liquid, especially if the product is not continuously shaken.

The present invention reduces and/or eliminates some of the aforementioned problems. In particular, the compositions of the present invention are able to provide two phase antiperspirants and/or deodorants which have improved efficacy, reduced irritation on skin, reduced white residue on skin and clothing, and improved aesthetics such as reduced wetness.

BRIEF SUMMARY OF THE INVENTION

This invention is a two phase, roll-on product made with a polar phase and a non-polar phase wherein a cosmetically active ingredient effective as an antiperspirant and/or a deodorant is dissolved or suspended in one of the phases. The composition is packaged in a conventional roll-on dispenser. Before the product is applied the container is shaken or agitated forcefully enough to temporarily mix the two phases. The product is applied while the two phases are mixed.

The non-polar phase can be clear, translucent or opaque, has a viscosity in the range of 20–9,000 centipoise, and is made by combining the following ingredients:
(a) a cross-linked or partially cross-linked non-emulsifying siloxane elastomer in an amount sufficient to provide a non-polar phase having a viscosity in the range of 20 centipoise ("cps")–9,000 cps, preferably 100–3000 cps and most preferably 240–350 cps (for example in an amount of 40–70 weight % of a 11–13% concentration of elastomer in a solvent, or an equivalent amount if a different concentration of elastomer is used);
(b) 0.1–70 weight % (more particularly 1–50% and, even more particularly 10–40%) of one or more low viscosity, lipophilic emollients selected from the group consisting of:
  (i) 0.1–40 weight % (preferably 10–40%) of a linear or cyclic volatile silicone;
  (ii) 0.1–20 weight % (with particular ranges being 0.1–2%, 0.1–3.5% and 2–8%) of a volatile, nonpolar hydrocarbon (preferably branched such as with an "iso" group) having from 4–30 carbons (preferably 4–20 carbons and, more preferably, 6–20 carbons);
  (iii) 0.1–20 weight % (particularly 2–10% and, more particularly, 3–5%) of a benzoic acid ester selected from the group consisting of C12–C20 benzoate esters (for example a C12–15 alkyl benzoate such as FIN-SOLV TN);
  (iv) 0.01–8 weight % of a propoxylated fatty alcohol having 4–16 carbons and 2–14 moles of propoxylation (for example, PPG-3 myristyl ether); and
(c) optionally one or more ingredients selected from the group consisting of fragrance (for example, 0.0 to 2 weight %, preferably from 0.5 to 1% ); vitamins (in amounts of 0.01–1.00 weight %) (especially vitamin E or a precursor); and a coloring agent (for example, a cosmetic pigment) in amounts of 0.05–0.5%.

The polar phase can be clear, translucent or opaque. In general it may contain one or more members selected from water and or a polyhydric alcohol wherein the cosmetically active ingredients are dissolved in this polar phase; The polar phase should also have a viscosity in the range of 20 cps–9,000 cps. The polar phase comprises:
(a) an effective amount (which shall be at least 5 weight %) of a cosmetically active ingredient soluble or suspendible in the polar phase, especially an antiperspirant active;
(b) a sufficient amount of a glycol or polyhydric alcohol to dissolve or suspend the antiperspirant active (or other cosmetic active) optionally containing up to 30 weight % water, or 16.00 weight % (maximum) ethyl alcohol, isopropyl alcohol, or mixtures thereof;
(c) 0.1–2.5 weight % of a water soluble cationic derivative selected from the group consisting of hydroxyethyl cellulose and its copolymers (preferably Polyquaternium-10 (Celquat SC 240 C from National Starch, Findeme, N.J.)), and hydroxypropyl cellulose and its copolymers, provided that the viscosity of the polar phase does not exceed 9,000 cps;
(d) optionally one or more ingredients selected from the group consisting of
  (i) micas ($\leq 1.0$ weight %, with an average particle size in the range of 10–125 microns and preferably less than 30 microns);
  (ii) suspending agents (for example 1–3 weight % of Bentone 38 with the addition of a polar additive, for example 0.3–1.0 weight % of propylene carbonate);
  (iii) antimicrobial agents (which may also be considered as a cosmetic ingredient if used in sufficient amount to inhibit bacteria growth under the arm), for example, a member of the group consisting of bacteriostatic quaternary ammonium compounds such as 2-amino-2-methyl-1-propanol (AMP), cetyl-trimethylammonium bromide, cetyl pyridinium chloride, 2,4,4'-trichloro-2'-hydroxydiphenylether (Triclosan), N-(4-chlorophenyl)-N'-(3,4-dichlorophenyl)urea (Triclocarban), silver halides, octoxyglycerin (Sensiva™ SC 50);3,7,11,-trimethyldodeca-2,6,10-trienol (Farnesol from Dragoco, Totowa, N.J.); and various zinc salts (for example, zinc ricinoleate). The bacteriostat can, illustratively, be included in the composition in an amount of 0–5%, particularly 0.01–1.0% by weight, of the total weight of the composition. Triclosan, can illustratively be included in an amount of from 0.05% to about 0.5% by weight, of the total weight of the composition.
  (iv) fragrances in an amount in the range of 0–5%, particularly 0.01–2.0%, and, for example, at a level of 1%;
  (v) masking agents in an amount of 0.05–5.0% (particularly 0.05–2%) by weight based on the total weight of the composition particularly if an unscented product is desired;
  (vi) polymers of ethylene oxide, for example PEG-4, PEG-6, PEG-8, PEG-9, PEG-10, PEG-12, PEG 14, Carbowax PEG-200, Carbowax PEG-300, Carbowax PEG-400, Carbowax PEG-600, particularly 0.1–1.0 weight % of PEG-12; and
  (vii) a cosmetically acceptable coloring agent in an amount of 0.0001–0.002 weight %) (for example, dyes approved for cosmetic use by the FDA and/or European regulatory agencies or legislation).

DETAILED DESCRIPTION OF THE INVENTION

The elastomer is a non-emulsifying polysiloxane that does not contain any appreciable amount of polyoxyalkylenes, for example, polyoxyethylenes, and may be selected from the group consisting of:

(a) a cross-linked or partially cross-linked cyclomethicone (and) dimethicone crosspolymer (for example, DC 9040 from Dow Corning Corp., Midland, Mich.);

(b) a cross-linked or partially cross-linked dimethicone/vinyldimethicone crosspolymer (for example, KSG-15 from Shin-Etsu Silicones of America, Akron Ohio);

(c) a cross-linked or partially cross-linked cyclomethicone (and) vinyldimethicone/methicone crosspolymer (for example, GE 1229 from General Electric Silicones, Waterford, N.Y.).

One particular type of elastomer is described in U.S. Pat. No. 5,654,362, incorporated by reference to the extent it defines non-emulsifying elastomers. These elastomers are prepared by a crosslinking reaction between (a)=Si—H containing polysiloxanes and (b) an alpha, omega-diene in the presence of a platinum catalyst and (c) a low molecular weight linear or cyclic polysiloxane. The elastomer can be swollen with the low molecular weight polysiloxane under a shear force. The=Si—H containing polysiloxane of part (a) is represented by compounds of formula $(R^{13})_3SiO(R^{14}_2SiO)_a(R^{15}HsiO)_bSi(R^{13})_3$, designated herein as type $A^1$, and compounds of the formula $H(R^{13})_2SiO(R^{14}_2SiO)_cSi(R^{13})_2H$ or formula $H(R^{13})_2SiO(R^{14}_2SiO)_a(R^{15}HsiO)_bSi(R^{13})_2H$, designated herein as $A^2$. In these formulas, $R^{13}$, $R^{14}$, and $R^{15}$ are alkyl groups with 1–6 carbon atoms, a is 0–250, b is 1–250, and c is 0–250. The molar ratio of compounds $A^1$:$A^2$ is 0–20, preferably 0–5. It is preferred that compounds of both types $A^1$ and $A^2$ be used. The alpha, omega diene in part (b) is a compound of the formula $CH_2=CH(CH_2)_xCH=CH_2$ where x is 1–20. Representative examples of suitable alpha, omega-dienes include 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

For the volatile silicones used in this invention, linear or cyclic materials may be used alone or in combination. Linear volatile methyl siloxanes ("VMS") have the formula $(CH_3)_3SiO\{(CH_3)_2SiO\}_ySi(CH_3)_3$. The value of y is 0–5. Cyclic VMS have the formula $\{(CH_3)_2SiO\}_z$. The value of z is 3–6. Preferably, these volatile methyl siloxanes have boiling points less than about 250 degrees C. and viscosities of about 0.65–5.0 centistokes ($mm^2/s$).

Representative linear volatile methyl siloxanes (I) are hexamethyldisiloxane (MM) with a boiling point of 100 degrees C., viscosity of 0.65 $mm^2/s$, and formula $Me_3SiOSiMe_3$; octamethyltrisiloxane (MDM) with a boiling point of 152 degrees C., viscosity of 1.04 $mm^2/s$, and formula $Me_3SiOMe_2SiOSiMe_3$; decamethyltetrasiloxane ($MD_2M$) with a boiling point of 194 degrees C., viscosity of 1.53 $mm^2/s$, and formula $Me_3SiO(Me_2SiO)_2SiMe_3$; dodecamethylpentasiloxane ($MD_3M$) with a boiling point of 229 degrees C., viscosity of 2.06 $mm^2/s$, and formula $Me_3SiO(Me_2SiO)_3SiMe_3$; tetradecamethylhexasiloxane ($MD_4M$) with a boiling point of 245 degrees C., viscosity of 2.63 $mm^2/s$, and formula $Me_3SiO(Me_2SiO)_4SiMe_3$; and hexadecamethylheptasiloxane ($MD_5M$) with a boiling point of 270 degrees C., viscosity of 3.24 $mm^2/s$, and formula $Me_3SiO(Me_2SiO)_5SiMe_3$.

Representative cyclic volatile methyl siloxanes (II) are hexamethylcyclotrisiloxane ($D_3$) a solid with a boiling point of 134 degrees C. and formula $\{(Me_2)SiO\}_3$; octamethylcyclotetrasiloxane ($D_4$) with a boiling point of 176 degrees C., viscosity of 2.3 $mm^2/s$, and formula $\{(Me_2)SiO\}_4$; decamethylcyclopentasiloxane ($D_5$) with a boiling point of 210 degrees C., viscosity of 3.87 $mm^2/s$, and formula $\{(Me_2)SiO\}_5$; and dodecamethylcyclohexasiloxane ($D_6$) with a boiling point of 245 degrees C., viscosity of 6.62 $mm^2/s$, and formula $\{(Me_2)SiO\}_6$ (with a particular group of cyclics including D5 and D6 cyclomethicones).

Particular examples of suitable volatile silicones include DC-244 Fluid, DC-245 Fluid, DC 246 Fluid, DC-344 Fluid, DC-345 Fluid, DC 200 Fluid (with 0.65 cst viscosity) to DC 200 Fluid (with 5 cst viscosity), and DC-1184 Fluid (a mixture of low molecullar weight volatile and non-volatile silicones most of which are linear and volatile, such material has a boiling point greater than 35 degrees and a viscosity of about 1.6 centistokes) all of which are from Dow Corning Corp.), and especially decamethylcyclopentasiloxane (DC-245 Fluid).

Hydrocarbons suitable for use in this invention include isoparaffinic fluids having 4–30 carbons (especially 7–20 carbons) such as C7–8 isoparaffin, C8–9 isoparaffin, C10–11 isoparaffin, C11–12 isoparaffin, C11–13 isoparaffin, C13–14 isoparaffin, C12–20 isoparaffin, especially C11–12 isoparaffin (for example, Isopar H from Exxon Chemical Company, Baytown, Tex.), and other branched chain hydrocarbons such as isododecane (Permethyl 99A), isoeicosane (Permethyl 102A), isohexadecane (Permethy 101A) (the Pernethyls being available from Preperse, Inc., South Plainfield, N.J.), and combinations of any of the foregoing.

Particular examples of benzoate esters which can be used in this invention include isostearyl benzoate, PPG-15 stearyl ether benzoate, octyldodecyl benzoate, and C12–15 alkyl benzoate and those described in U.S. Pat. Nos. 4,791,097 and 5,270,461, incorporated by reference herein with respect to the description of such esters. These include compositions of formula:

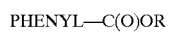

where R is:

(a) a branched or linear alkyl of 20–28 carbons; or (b) $-CH(CH_3)-CH_2(O-CH(CH_3)CH_2)_n-O-R^1$, wherein n is 9–16 and $R^1$ is a branched or linear alkyl of 3–22 carbons.

More particular examples of such benzoate esters include isostearyl benzoate, PPG-15 stearyl ether benzoate, octyldodecyl benzoate, and C12–15 alkyl benzoate (for example and preferably, Finsolv TN from Finetex, Inc. (Elmwood Park, N.J.).

Another particular group of such esters include those marketed by Finetex under the designations FINSOLV® TN (C12–15 alkyl benzoate), FINSOLV® SB (isostearyl benzoate), FINSOLV® P (PPG-15 stearyl ether benzoate), FINSOLV® BOD (octyl dodecyl benzoate), FINSOLV® 116 (stearyl benzoate), FINSOLV® PL-62 (Poloxamer 182 benzoate) and FINSOLV® PL-355 (poloxamer 105 benzoate).

The antiperspirant active can be selected from the group consisting of any of the known antiperspirant active materials. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Particular types of antiperspirant actives include aluminum zirconium trichlorohydrex and aluminum zirconium tetrachlorohydrex either with or without glycine. A particular antiperspirant active is aluminum trichlorohydrex gly such as AZZ-902 SUF (from Reheis Inc., Berkley Heights, N.J.) which has 98% of the particles less than 10 microns in size.

Antiperspirant actives can be incorporated into compositions according to the present invention in amounts in the range of 0.1–25% of the final composition, but the amount used will depend on the formulation of the composition. For example, at amounts in the lower end of the broader range (for example, 0.1–10% on an actives basis), a deodorant effect may be observed. At lower levels the antiperspirant active material will not substantially reduce the flow of perspiration, but will reduce malodor, for example, by acting as an antimicrobial material. At amounts of 10–25% (on an actives basis) such as 15–25%, by weight, of the total weight of the composition, an antiperspirant effect may be observed.

The glycol or polyglycol is selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component include one or more members of the group consisting of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Propylene glycol is of particular interest because the antiperspirant active is more soluble in this type of glycol. Tripropylene glycol has lower irritancy, but the antiperspirant active is not as soluble in this glycol. Mixtures of glycols may be used to balance these desirable properties.

Compositions according to the present invention can be made by first preparing both phases separately and then combining them in the final container:

Non-polar phase—The emollients are blended at room temperature in a vessel and added slowly to the silicone elastomer with agitation so as to form an homogeneous mixture free of lumps. Optionally, fragrances can be added at the end.

Polar phase—If the polar phase contains a copolymer of hydroxyethyl cellulose, this is dissolved in the solution or suspension of the active ingredient with vigorous agitation so as to form a clear solution free of lumps.

If a coloring agent is added, it is first dissolved in a selected amount of polar material such as water, or in a nonpolar material such as polydimethylsiloxane (for example, DC 200 Fluid having a viscosity of 5 centistokes ("cst"); DC 200 Fluid having a viscosity of 50 cst, both of which are available from Dow Corning Corp.) and then added to the appropriate phase.

Each phase can be introduced into dispensing containers known to those skilled in the art for roll-ons. The product from the reservoir comes to the top rolling surface of the dispensing container, and from there may be applied to the skin in the axillary regions to deposit sufficient amounts of antiperspirant and/or deodorant active material to reduce body malodor and/or reduce perspiration in axillary regions of the human body.

The components of the conventional roll-on containers can be made of various materials and can have different shapes. The material of the container can be polypropylene, polyethylene terephthalate (PET), high-density polyethylene or glass. The applicator is usually a hollow ball made of polypropylene. The diameter can vary from 10.4 to 35.5 mm, depending on the design of the container. The ball can be assembled directly in the container or with a special insert (ball housing) depending also on the design of the container. The caps can be of different designs (usually made of polypropylene) with smooth or ribbed walls.

Examples of suitable roll-on dispensers include those described in U.S. Des. Pat. No. 402,550 to Poisson; U.S. Pat. No. 6,132,126 to Sheffer et al (an adjustable applicator);U.S. Pat. No. 4,030,844 to Lench et al; U.S. Pat. No. 4,021,125 to Berghahn et al; U.S. Pat No. 4,033,700 to Spatz; U.S. Pat. No. 5,553,957 to Dombusch et al; WO 00/64302 to Hindustan Lever Ltd.; and WO 01/03541 to Chang; all of which are incorporated by reference herein to the extent they describe roll-on dispensers.

Various forms of the invention can be exemplified by the following formulations but these should not be construed as limitations on the invention. Note that where an amount of an elastomer is given which references a certain concentration, it will be understood that other amounts of other concentrations maybe be used provided that the amount of elastomer is kept in the same range.

Formulation A

Non-polar Phase

22–35 weight % elastomer in cyclomethicone (DC 9040 elastomer from Dow Corning Corp.) (using a concentration of 11–13 weight % elastomer in cyclomethicone)

15–20 weight % isoparaffinic fluid (ISOPAR H from Exxon-Mobil Chemical, Houston, Tex.)

3–5 weight % C12–15 alkyl benzoate (FINSOLV TN)

Polar Phase

39–59.5 weight % of Al Zr tetrachlorohydrex gly (30% in propylene glycol solution (REACH AZP 908, from Reheis))

0.5–1.0 (optionally) fragrance.

Formulation B

Non-polar Phase

22–32 weight % elastomer in cyclomethicone (DC 9040 elastomer from Dow Corning Corp.) (using a concentration of 11–13 weight % elastomer in cyclomethicone)

14–20 weight % cyclomethicone (DC 245 Fluid from Dow Corning Corp.)

3–5 weight % C12–15 alkyl benzoate (FINSOLV TN)
1–3 weight % PPG-3 myristyl ether from (Croda Oleochemicals Inc. Parsippany, N.J.)
Polar Phase
  39–58 weight % of Al Zr tetrachlorohydrex gly (30% in water and propylene glycol where propylene glycol is in the range of 20–25% of the total weight of the active (Z498 from Summit))
  0.5–1.0 weight % Polyquaternium 10 (Celquat SC 240 C from National Starch, Findeme, N.J.)
  0.5–1.0 weight % (optionally) fragrance.
Formulation C
Non-polar Phase
  25–35 weight % elastomer in cyclomethicone (DC 9040 elastomer from Dow Corning Corp.) (using a concentration of 11–13 weight % elastomer in cyclomethicone)
  14–20 weight % polydimethylsiloxane ( DC 1184 Fluid from Dow Corning Corp.)
  0.5–2 weight % C12–15 alkyl benzoate (FINSOLV TN)
  0.5–3 weight % PPG-3 myristyl ether (Croda Oleochemicals Inc.)
Polar Phase
  39–58 weight % of Al Zr tetrachlorohydrex gly (35% in water and propylene glycol, where propylene glycol is in the range of 20–25% of the total weight of the active (Z498 from Summit))
  0.5–1.0 weight % Polyquaternium 10 (Celquat SC 240 C)
  0.5–1.0 weight % (optionally) fragrance.
Formulation D
Non-polar Phase
  25–35 weight % elastomer in cyclomethicone (DC 9040 elastomer from Dow Corning Corp.) (using a concentration of 11–13 weight % elastomer in cyclomethicone)
  14–21 weight % polydimethylsiloxane (DC 200 Fluid with a viscosity of 0.65 cst from Dow Corning Corp.)
  1.0–3 weight % C12–15 alkyl benzoate (FINSOLV TN)
  0.5–1 weight % PPG-3 myristyl ether from (Croda Oleochemicals Inc)
Polar Phase
  39.5–58.5 weight % of Al Zr tetrachlorohydrex gly (30% in PG solution, REACH AZP 908)
  0.5–1.0 weight % (optionally) fragrance.
Formulation E
Non-polar Phase
  29–38 weight % elastomer in cyclomethicone (DC 9040 elastomer from Dow Corning Corp.) (using a concentration of 11–13 weight % elastomer in cyclomethicone)
  12–20 weight % cyclomethicone (DC 246 Fluid from Dow Corning Corp.)
  0.5–3 weight % PPG-14 butyl ether (Fluid AP from Amerchol, Edison, N.J.)
Polar Phase
  38.5–57.5 weight % of Al Zr tetrachlorohydrex gly (30% in propylene glycol, REACH AZP 908 from Reheis)
  0.5–1.0 weight % (optionally) fragrance.
Formulations F, G and H
  Any of the formulations in Formulation B, C or D wherein the amount of C12–15 alkyl benzoate is 3% and the amount of PPG-3-myristyl ether is 1%.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application (a) values for n, m, etc. in formulas, molecular weights and degree of ethoxylation or propoxylation are averages; (b) temperatures are in degrees C unless otherwise indicated; and (c) the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997). Mixing techniques used to make the compositions are those conventionally used in the art including those described above.

Examples 1–6

General Method of Making Compositions

Compositions according to the present invention as seen in Examples 1–6 may be made as follows using the amounts and types of ingredients listed under the appropriate Example number. Total percent for each Example is 100%

Non-polar phase—The cyclomethicone and the emollients (hydrocarbons, benzoate esters, ethers) are blended at room temperature and added slowly to the silicone elastomer with stirring to form an homogeneous mixture free of lumps. If the final formulation is to be made with a cosmetic pigment for example, mica, titanium dioxide, or iron oxide), the pigment must be pre-dispersed in a polydimethyl siloxane. If the final formulation contains a fragrance in the non-polar phase, the fragrance will be added in this phase at the end.

Polar phase—If the polar phase contains a modified starch (such as hydroxypropyl starch phosphate starch), it must be pre-dispersed in a small part of the antiperspirant active, then heated at 75 degrees C. until the starch is dissolved to form a solution. The pre-dispersed material is then added to the rest of the antiperspirant active with agitation until it is cooled to room temperature. If the polar phase contains a suspending agent (for example, a Hectorite material), it must be added with high shear to the Al Zr tetrachlorohydrex gly in propylene glycol (for example, 30% solution or its equivalent) until the mixture is uniform. After this happens the propylene carbonate may be added. If the polar contains Polyquaternium 10, this is pre-dispersed in the active to form an homogeneous solution free of lumps. If the final formulation contains a colorant is must be dissolved in the minimum amount of water and then added in the polar phase.

Combination of the phases in a container—Each phase is poured into the container in the ratios indicated in the final composition. There is no special order of addition into the container. The polar phase will tend to go to the bottom.

The method described above was used to make the following compositions wherein all amounts are weight % based on the total weight of the composition.

Example 1

Non-polar phase
  28.0% elastomer (DC 9040 crosslinked silicone elastomer)
  18.0% pentameric cyclomethicone (DC 245 Fluid)
  3.0% C12–15 alkyl benzoate (Finsolv TN)
  1.0% polyoxypropylene-3 myristyl ether (Promyristyl PM3)
Polar phase 50.0% Al Zr tetrachlorohydrex gly (30% active in propylene glycol) (AZP 908 PG 30 from Reheis Inc.)

Example 2

Non-polar phase 28.0% elastomer (DC 9040 crosslinked silicone elastomer)

18.0% pentameric cyclomethicone (DC 245 Fluid)

3.0% C11–12 isoparaffin (Isopar H)

1.0% polyoxypropylene-3 myristyl ether (Promyristyl PM3)

Polar phase 50.0% Al Zr tetrachlorohydrex gly (30% active in propylene glycol) (AZP 908 PG 30)

Example 3

Non-polar phase 28.0% elastomer (DC 9040 crosslinked silicone elastomer)

17.997% pentameric cyclomethicone (DC 245 Fluid)

3.0% C12–15 alkyl benzoate (Finsolv TN)

1.0% polyoxypropylene-3 myristyl ether (Promyristyl PM3)

0.003% mica (Timiron MP-99 Sunflake from Merck, Whitehouse, N.J.)

Polar phase 50.0% Al Zr tetrachlorohydrex gly (30% active in propylene glycol) (AZP 908 PG 30)

0.25% hydroxypropyl starch phosphate starch (Structure Solanance 28-1808, from National Starch)

Example 4

Non-polar phase 28.0% elastomer (DC 9040 crosslinked silicone elastomer)

18.0% pentameric cyclomethicone (DC 245 Fluid)

3.0% C11–12 isoparaffin (Isopar H)

1.0% polyoxypropylene-3 myristyl ether (Promyristyl PM3 from Croda)

Polar phase 48.0% Al Zr tetrachlorohydrex gly (30% active) (AZP 908 PG 30)

1.5% Quaternium-18 hectorite (Bentone 38 from Rheox Inc.)

0.5% propylene carbonate q.s. mica (Timiron MP-99 Sunflake from Merck)

Example 5

Non-polar phase 22.4% elastomer (DC 9040 crosslinked silicone elastomer)

14.4% pentameric cyclomethicone (DC 245 Fluid from Dow Corning Corp.)

2.4% C12–15 alkyl benzoate (Finsolv TN)

0.8% polyoxypropylene-3 myristyl ether (Promyristyl PM3)

Polar phase 59.699% Al Zr tetrachlorohydrex gly (35% water and propylene glycol solution (Z-535 from Summit))

0.3% Polyquaternium 10 (Celquat SC 240 C from National Starch)

0.0002% FD&C color

Example 6

Non-polar phase 25.2% elastomer (DC 9040 crosslinked silicone elastomer)

16.2% pentameric cyclomethicone (DC 245 Fluid)

2.7% C12–15 alkyl benzoate (Finsolv TN)

0.9% polyoxypropylene-3 myristyl ether (Promyristyl PM3)

Polar phase 54.725% Al Zr tetrachlorohydrex gly (35% water and propylene glycol solution (Z-535 from Summit))

0.275% Polyquaternium 10 (Celquat SC 240C)

Evaluation of Examples 1–4

Example 1—Two transparent phases were formed with a suitable viscosity to flow through a wide ball (3.5 cm) roll-on package. The product was laid on a flat surface overnight to evaluate possible leakage. This Example did not exhibit any leakage.

Example 2—The non-polar phase was semi-turbid. The product had a viscosity suitable for the wide ball package described for Example 1. The product had a non-tacky but slightly greasy feel.

Example 3—This formulation exhibited a typical two phase separation. The polar phase with the active ingredient was turbid due to the presence of the starch that was used to increase the viscosity of the active ingredient solution and to improve the mica suspension in the formulation. It was found that the starch decreased the tackiness of the active. The overall formulation was perceived as non-tacky, silky and had a dry feel after application. However, the mica suspension was not stable after 3 days. It is believed that mica with a smaller particle size (for example, less than 30 microns) would result in a more stable product.

Example 4—The formation of two phases was observed as described for Example 3. The polar phase with the active was not clear. In this formulation the Hectorite material was used as a suspending agent instead of the modified starch to improve the suspension of the mica. In order to achieve a good dispersion of the Hectorite 18 material, a polar solvent (propylene carbonate) was used. The prototype was perceived as somewhat tacky and slightly greasy. The Isopar H and the propylene carbonate may have caused the greasy feel. The mica suspension was not stable because both the Hectorite 18 and the mica settled out after 24 hours. Again, an adjustment to a smaller particle size may improve stability.

Example 5—Two transparent phases were formed with a suitable viscosity (estimated to be in the range of 100–200 cps) to flow through the ball applicator described in the evaluation of Example 1. The color of the polar phase was blue and uniform. It maintained its integrity after shaking. The product was perceived as nontacky, non-greasy, silky and with a dry feel after application.

Example 6—Two transparent phases were formed with a suitable viscosity (estimated to be in the range of 100–200 cps) to flow through the ball applicator described in the evaluation of Example 1. The product was perceived as non-tacky, non-greasy, silky and with a dry feel after application.

What is claimed is:

1. A two-phase roll-on antiperspirant and/or deodorant comprising (a) a clear, translucent or opaque non-polar phase having a viscosity in the range of 20 cps–9,000 cps made by combining:
  (1) a cross-linked or partially cross-linked non-emulsifying siloxane elastomer in an amount sufficient to provide a non-polar phase having a viscosity in the range of 20–9,000 cps;
  (2) 0.1–70 weight % of one or more lipophilic emollients selected from the group consisting of:
    (i) 0.1–40 weight % of a linear or cyclic volatile silicone;
    (ii) 0.1–20 weight % of a volatile, nonpolar hydrocarbon having from 4–30 carbons;
    (iii) 0.1–20 weight % of a benzoic acid ester selected from the group consisting of C12–C20 benzoate esters;
    (iv) 0.01–8 weight % of a propoxylated fatty alcohol having 4–16 carbons and 2–14 moles of propoxylation; and
  (3) optionally one or more ingredients selected from the group consisting of fragrance; vitamins; and pigments, and coloring agents; and
(b) a clear, translucent or opaque polar phase having a viscosity in the range of 20–9,000 cps made by combining:
  (1) one or more members selected from the group consisting of water, glycols and polyhydric alcohols; and
  (2) an antiperspirant active salt which is soluble or suspendible in the polar phase; wherein the polar phase (i) comprises a sufficient amount of water, glycols or polyhydric alcohols to dissolve or suspend the antiperspirant active, and (ii) optionally may comprise up to 30 weight % water; up to 16.00 weight % ethyl alcohol; up to 16 weight % isopropyl alcohol; or mixtures or any of the foregoing;
  (3) 0.1–2.5 weight % of a water soluble cationic derivative selected from the group consisting of hydroxyethyl cellulose and its copolymers; and
(c) optionally one or more ingredients selected from the group consisting of
  (i) ≦1.0 weight % of mica with an average particle size in the range of 10–125 microns;
  (ii) an effective amount of a suspending agent;
  (iii) an antimicrobial agent;
  (iv) fragrance;
  (v) 0.05–5.0 weight % of a masking agent;
  (vi) 0.1–1.0 weight % of a polymer of ethylene oxide; and
  (vii) a cosmetically acceptable coloring agent.

2. A two-phase roll-on antiperspirant and/or deodorant according to claim 1 wherein the elastomer has a viscosity in the range of 100–3000 cps.

3. A two-phase roll-on antiperspirant and/or deodorant according to claim 1 wherein the elastomer has a viscosity in the range of 240–350 cps.

4. A two-phase roll-on antiperspirant and/or deodorant according to claim 1 wherein the elastomer has a viscosity in the range of 100–200 cps.

5. A two-phase roll-on antiperspirant and/or deodorant according to claim 1 comprising (a) 40–70 weight % of a combination of elastomer and one or more lipophilic emollients, wherein the concentration of elastomer in the combination is in the range of 11–13%; or (b) a combination of elastomer and one or more low viscosity, lipophilic emollients wherein the total amount of elastomer is equivalent to the amount of elastomer in (a).

6. A two-phase roll-on antiperspirant and/or deodorant according to claim 1 or claim 5 wherein the elastomer is prepared by a crosslinking reaction between (a) =Si—H containing polysiloxanes and (b) an alpha, omega-diene in the presence of a platinum catalyst and (c) a linear or cyclic polysiloxane.

7. A two-phase roll-on antiperspirant and/or deodorant according to claim 1 or claim 5 wherein the elastomer is prepared by a crosslinking reaction between (a) =Si—H containing polysiloxanes and (b) an alpha, omega-diene in the presence of a platinum catalyst and (c) a linear or cyclic polysiloxane; the =Si—H containing poly-siloxane of part (a) is a compound of formula $(R^{13})_3SiO(R^{14}{}_2SiO)_a(R^{15}HSiO)_bSi(R^{13})_3$, designated herein as type $A^1$, and compounds of the formula $H(R^{13})_2SiO(R^{14}{}_2SiO)_cSi(R^{13})_2H$ or formula $H(R^{13})_2SiO(R^{14}{}_2SiO)_a(R^{15}HSiO)_bSi(R^{13})_2H$, designated herein as $A^2$, for which $R^{13}$, $R^{14}$, and $R^{15}$ are alkyl groups with 1–6 carbon atoms, a is 0–250, b is 1–250, and c is 0–250; the molar ratio of compounds $A^1:A^2$ is 0–20; and the alpha, omega diene in part (b) is a compound of the formula $CH_2=CH(CH_2)_xCH=CH_2$ where x is 1–20.

8. A two-phase roll-on antiperspirant and/or deodorant according to claim 1 wherein the elastomer is selected from the group consisting of:
  (a) a cross-linked or partially cross-linked cyclomethicone (and) dimethicone crosspolymer;
  (b) a cross-linked or partially cross-linked dimethicone/vinyldimethicone crosspolymer; and
  (c) a cross-linked or partially cross-linked cyclomethicone (and) vinyldimethicone/methicone crosspolymer.

9. A two-phase roll-on antiperspirant and/or deodorant according to claim 1 comprising 1–50 weight % of one or more lipophilic emollients.

10. A two-phase roll-on antiperspirant and/or deodorant according to claim 1 comprising 10–40 weight % of one or more lipophilic emollients.

11. A two-phase roll-on antiperspirant and/or deodorant according to any one of claim 1 or 5, wherein the lipophilic emollient comprises 10–40 weight % of a linear or cyclic volatile silicone.

12. A two-phase roll-on antiperspirant and/or deodorant according to claim 1 wherein the lipophilic emollient comprises 0.1–20 weight % a volatile, nonpolar hydrocarbon which is branched with an iso group and has 4–30 carbons.

13. A two-phase roll-on antiperspirant and/or deodorant according to claim 1 wherein the lipophilic emollient comprises 0.1–2 weight % a volatile, nonpolar hydrocarbon which is branched with an iso group and has 4–30 carbons.

14. A two-phase roll-on antiperspirant and/or deodorant according to claim 1 wherein the lipophilic emollient comprises 0.1–2 weight % a volatile, nonpolar hydrocarbon which is branched with an iso group and has 6–20 carbons.

15. A two-phase roll-on antiperspirant and/or deodorant according to claim 1 wherein the lipophilic emollient comprises 0.1–20 weight % of a benzoic acid ester selected from the group consisting of C12–C20 benzoate esters.

16. A two-phase roll-on antiperspirant and/or deodorant according to claim 1 wherein the lipophilic emollient comprises 2–10 weight % of a benzoic acid ester selected from the group consisting of C12–C20 benzoate esters.

17. A two-phase roll-on antiperspirant and/or deodorant according to claim 1 wherein the lipophilic emollient comprises 0.01–8 weight % of a propoxylated fatty alcohol having 4–16 carbons and 2–14 moles of propoxylation.

18. A two-phase roll-on antiperspirant and/or deodorant according to claim 17 wherein the lipophilic emollient comprises 0.01–8 weight % PPG-3 myristyl ether.

19. A two-phase roll-on antiperspirant and/or deodorant according to claim 1 wherein the lipophilic emollient comprises 0.1–20 weight % of a benzoic acid ester selected from the group consisting of C12–C20 benzoate esters and 0.01–8 weight % of a propoxylated fatty alcohol having 4–16 carbons and 2–14 moles of propoxylation.

20. A two-phase roll-on antiperspirant and/or deodorant according to claim 1 additionally comprising at least one member from the group consisting of up to 2 weight % fragrance; 0.01–1.00 weight % vitamins; and 0.05–0.5 weight % coloring agent.

21. A two-phase roll-on antiperspirant and/or deodorant according to claim 20 wherein the coloring agent is a pigment.

22. A two-phase roll-on antiperspirant and/or deodorant according to claim 1 wherein the suspending agent is 1–3 weight % of Quaternium-18 hectorite with 0.3–1.0 weight % propylene carbonate.

23. A two-phase roll-on antiperspirant and/or deodorant according to claim 1 wherein the antiperspirant active salt is selected from the group consisting of aluminum chlorohydrate, aluminum chloride, aluminum sesquichlorohydrate, zirconyl hydroxychloride, aluminum-zirconium glycine complex, aluminum chlorohydrex propylene glycol, aluminum chlorohydrex polyethylene glycol, aluminum dichlorohydrex propylene glycol, and aluminum dichlorohydrex polyethylene glycol.

24. A two-phase roll-on antiperspirant and/or deodorant according to claim 1 wherein the antiperspirant active salt is selected from the group consisting of aluminum nitratohydrate, aluminum nitratohydrate and its combination with zirconyl hydroxychlorides and nitrides, and aluminum-stannous chlorohydrates.

25. A two-phase roll-on antiperspirant and/or deodorant according to claim 1 wherein the antiperspirant active salt is selected from the group consisting of aluminum zirconium trichlorohydrex and aluminum zirconium tetrachlorohydrex either with or without glycine.

26. A two-phase roll-on antiperspirant and/or deodorant according to claim 1 wherein the antiperspirant active salt is added in an amount in the range of 0.1–25 weight % of the final composition.

27. A two-phase roll-on antiperspirant and/or deodorant according to claim 1 wherein the antiperspirant active salt is added in an amount in the range of 10–25 weight % of the final composition.

28. A two-phase roll-on antiperspirant and/or deodorant according to claim 1 additionally comprising an antimicrobial agent selected from the group consisting of 2-amino-2-methyl-1-propanol; cetyl-trimethylammonium bromide; cetyl pyridinium chloride; 2,4,4'-trichloro-2'-hydroxydiphenylether; N-(4-chlorophenyl)-N'-(3,4-dichlorophenyl)urea; silver halides; octoxyglycerin; 3,7,11,-trimethyldodeca-2,6,10-trienol; and zinc salts.

29. A two-phase roll-on antiperspirant and/or deodorant according to claim 1 additionally comprising a masking agents in an amount of 0.05–5.0 weight %.

30. A two-phase roll-on antiperspirant and/or deodorant according to claim 1 additionally comprising a polymer of ethylene oxide selected from the group consisting of PEG-4, PEG-6, PEG-8, PEG-9, PEG-10, PEG-12, and PEG 14.

31. A two-phase roll-on antiperspirant and/or deodorant according to claim 1 wherein both the non-polar and polar phases are clear.

32. A two-phase roll-on antiperspirant and/or deodorant according to claim 1 wherein one of the non-polar and polar phases is clear.

33. A two-phase roll-on antiperspirant and/or deodorant according to claim 1 comprising the equivalent of 22–35 weight % elastomer in cyclomethicone at a 11–13% concentration of elastomer; 15–20 weight % isoparaffinic fluid; 3–5 weight % C12–15 alkyl benzoate; 39–59.5 weight % of Al Zr tetrachlorohydrex gly (30% in propylene glycol solution or its equivalent); and optionally 0.5–1.0 fragrance.

34. A two-phase roll-on antiperspirant and/or deodorant according to claim 1 comprising the equivalent of 22–35 weight % elastomer in cyclomethicone at a 11–13% concentration of elastomer; 3–5 weight % C12–15 alkyl benzoate; 1–3 weight % PPG-3 myristyl ether; 39–58 weight % of Al Zr tetrachlorohydrex gly (30% in water and propylene glycol where propylene glycol is in the range of 20–25% of the total weight of the active); 0.5–1.0 Polyquaternium 10; and optionally 0.5–1.0 fragrance.

35. A two-phase roll-on antiperspirant and/or deodorant according to claim 1 comprising the equivalent of 25–35 weight % elastomer in cyclomethicone at a concentration of 11–13% of elastomer; 14–20 weight % polydimethylsiloxane; 0.5–2 weight % C12–15 alkyl benzoate; 0.5–3 weight % PPG-3 myristyl ether; 39–58 weight % of Al Zr tetrachlorohydrex gly (35% in water and propylene glycol, where propylene glycol is in the range of 20–25 weight % of the total weight of the active); 0.5–1.0 weight % Polyquaternium 10; and optionally 0.5–1.0 weight % fragrance.

36. A two-phase roll-on antiperspirant and/or deodorant according to claim 1 comprising 25–35 weight % elastomer in cyclomethicone at a concentration of 11–13% of elastomer; 14–21 weight % polydimethylsiloxane; 1.0–3 weight % C12–15 alkyl benzoate; 0.5–1 weight % PPG-3 myristyl ether; 39.5–58.5 weight % of Al Zr tetrachlorohydrex gly (30% in propylene glycol solution or its equivalent); and optionally 0.5–1.0 weight fragrance.

37. A two-phase roll-on antiperspirant and/or deodorant according to claim 1 comprising 29–38 weight % elastomer in cyclomethicone at a concentration of 11–13% of elastomer; 12–20 weight % cyclomethicone; 0.5–3 weight % PPG-14 butyl ether; 38.5–57.5 weight % of Al Zr tetrachlorohydrex gly (30% in propylene glycol solution or its equivalent); optionally 0.5–1.0 weight % fragrance.

38. A two-phase roll-on antiperspirant and/or deodorant according to any one of claim 35, 36 or 37 wherein the amount of C12–15 alkyl benzoate is about 3 weight % and the amount of PPG-3-myristyl ether is about 1 weight %.

* * * * *